(12) United States Patent
Stump et al.

(10) Patent No.: US 11,386,390 B2
(45) Date of Patent: Jul. 12, 2022

(54) CENTRAL FILL FACILITY AND ASSOCIATED DRUG DISPENSING SYSTEM AND METHOD

(71) Applicant: McKesson Corporation, San Francisco, CA (US)

(72) Inventors: Bradley Stump, Atlanta, GA (US); Anujit Sen, Freemont, CA (US); Terese Baugh, Fort Worth, TX (US); Shubhangi Joshi, Alpharetta, GA (US); Richard Selby, Atlanta, GA (US); Seth Phillips, Atlanta, GA (US); Steve Maxwell, Lucas, TX (US); Andrew Maurer, Atlanta, GA (US)

(73) Assignee: MCKESSON CORPORATION, Irving, TX (US)

( * ) Notice: Subject to any disclaimer, the term of this patent is extended or adjusted under 35 U.S.C. 154(b) by 748 days.

(21) Appl. No.: 15/476,091

(22) Filed: Mar. 31, 2017

(65) Prior Publication Data
US 2018/0121867 A1    May 3, 2018

Related U.S. Application Data

(60) Provisional application No. 62/415,942, filed on Nov. 1, 2016.

(51) Int. Cl.
*G06Q 10/08* (2012.01)
*G16H 20/13* (2018.01)

(52) U.S. Cl.
CPC ......... *G06Q 10/087* (2013.01); *G06Q 10/083* (2013.01); *G16H 20/13* (2018.01)

(58) Field of Classification Search
CPC ........... G06Q 50/22–24; G06Q 10/087; G06Q 10/083; G16H 20/13

(Continued)

(56) References Cited

U.S. PATENT DOCUMENTS 6,343,711 B1    2/2002    Coughlin
6,370,215 B1    4/2002    Pinto et al.
(Continued)

FOREIGN PATENT DOCUMENTS

CA    2814259 A1 *    3/2001    ............... G07F 5/18

OTHER PUBLICATIONS

Farris, et al., "Population-Based Medication Reviews: A Descriptive Analysis of the Medication Issues Identified in a Medicare Not-for-Profit Prescription Discount Program", The Annals of Pharmacotherapy, Nov. 2004, vol. 38, pp. 1823-1829. (Year: 2004).*

*Primary Examiner* — Amber A Misiaszek
(74) *Attorney, Agent, or Firm* — Alston & Bird LLP (57) ABSTRACT

A central fill facility, drug dispensing system and method are provided in order to efficiently and accurately dispense a plurality of different drugs. The drug dispensing system includes a storage system configured to store a plurality of different drugs including a co-located inventory of a respective drug having both a first portion of the inventory of the respective drug to be dispensed pursuant to a predefined program and a second portion of the inventory of the respective drug that is not to be dispensed pursuant to the predefined program. The drug dispensing system also includes the dispensing station and dispensing control circuitry. The dispensing control circuitry is configured to control the dispensing station such that the first portion of the respective predefined program eligible drug is dispensed prior to dispensing the second portion of the respective predefined program ineligible drug.

10 Claims, 4 Drawing Sheets

(58) Field of Classification Search
USPC .......................................................... 705/2–3
See application file for complete search history.

(56) References Cited

U.S. PATENT DOCUMENTS

| | | | |
|---|---|---|---|
| 6,497,339 B1 | 12/2002 | Geltser et al. | |
| 6,564,121 B1 | 5/2003 | Wallace et al. | |
| 6,631,826 B2 | 10/2003 | Pollard et al. | |
| 6,684,914 B2 | 2/2004 | Gershman et al. | |
| 6,735,497 B2 | 5/2004 | Wallace et al. | |
| 6,892,512 B2 | 5/2005 | Rice et al. | |
| 6,898,919 B2 | 5/2005 | Kim | |
| 6,957,126 B2 | 10/2005 | Kim | |
| 6,970,769 B2 | 11/2005 | Rice et al. | |
| 6,971,541 B2 | 12/2005 | Williams et al. | |
| 6,983,579 B2 | 1/2006 | Rice et al. | |
| 7,080,755 B2 | 7/2006 | Handfield et al. | |
| 7,185,477 B2 | 3/2007 | Rice et al. | |
| 7,344,049 B2 | 3/2008 | Daniels et al. | |
| 7,383,862 B2 | 6/2008 | Geltser et al. | |
| 7,412,814 B2 | 8/2008 | Rice et al. | |
| 7,430,838 B2 | 10/2008 | Rice et al. | |
| 7,454,261 B2 | 11/2008 | Kim | |
| 7,584,018 B2 | 9/2009 | Shows et al. | |
| 7,640,170 B1 * | 12/2009 | Gourley | G16H 40/67 |
| | | | 705/2 |
| 7,668,618 B2 | 2/2010 | Szesko et al. | |
| 7,703,637 B2 | 4/2010 | Michelli | |
| 7,721,914 B2 | 5/2010 | Handfield et al. | |
| 7,805,216 B2 | 9/2010 | Shows et al. | |
| 7,832,591 B2 | 11/2010 | Karwacki, Jr. et al. | |
| 7,837,061 B2 | 11/2010 | Dummer et al. | |
| 7,866,506 B2 | 1/2011 | Daniels et al. | |
| 7,870,973 B2 | 1/2011 | Michelli et al. | |
| 7,909,207 B2 | 3/2011 | Handfield et al. | |
| 7,949,426 B2 | 5/2011 | Handfield et al. | |
| 7,949,427 B2 | 5/2011 | Michelli et al. | |
| 7,970,490 B2 | 6/2011 | Fellows et al. | |
| 7,988,017 B2 | 8/2011 | Kulberg et al. | |
| 8,016,095 B2 | 9/2011 | Daniels et al. | |
| 8,020,724 B2 | 9/2011 | Remis et al. | |
| 8,054,086 B2 | 11/2011 | Rivenbark, Jr. | |
| 8,061,560 B2 | 11/2011 | Farnsworth et al. | |
| 8,121,725 B2 | 2/2012 | Baker et al. | |
| 8,136,332 B2 | 3/2012 | Rice et al. | |
| 8,180,484 B2 | 5/2012 | Baker et al. | |
| 8,240,506 B2 | 8/2012 | Kulberg et al. | |
| 8,244,401 B2 | 8/2012 | Michelli et al. | |
| 8,261,936 B2 | 9/2012 | DuMond et al. | |
| 8,271,128 B1 | 9/2012 | Schultz | |
| 8,275,481 B2 | 9/2012 | Rice et al. | |
| 8,281,955 B2 | 10/2012 | Farnsworth et al. | |
| 8,340,809 B2 | 12/2012 | Chadbourne | |
| 8,412,538 B2 * | 4/2013 | Hardaway | G06Q 20/203 |
| | | | 705/2 |
| 8,428,775 B2 | 4/2013 | Baker et al. | |
| 8,434,641 B2 | 5/2013 | Coughlin et al. | |
| 8,464,901 B2 | 6/2013 | Karwacki, Jr. et al. | |
| 8,467,899 B2 | 6/2013 | Karwacki, Jr. et al. | |
| 8,499,967 B2 | 8/2013 | Michelli | |
| 8,616,409 B2 | 12/2013 | Young et al. | |
| 8,651,320 B2 | 2/2014 | DuMond et al. | |
| 8,651,326 B2 | 2/2014 | Pollard et al. | |
| 8,714,405 B2 | 5/2014 | Farnsworth et al. | |
| 8,774,964 B2 | 7/2014 | Shows et al. | |
| 8,777,055 B2 | 7/2014 | Farnsworth et al. | |
| 8,813,997 B2 | 8/2014 | Karwacki, Jr. et al. | |
| 8,833,604 B2 | 9/2014 | Karwacki, Jr. et al. | |
| 8,855,811 B1 | 10/2014 | Schultz | |
| 8,896,322 B2 | 11/2014 | Rivenbark, Jr. | |
| 8,972,047 B2 | 3/2015 | Johnson et al. | |
| 8,972,050 B2 | 3/2015 | Johnson et al. | |
| 9,147,044 B2 | 9/2015 | Shows et al. | |
| 9,241,875 B2 | 1/2016 | Davis et al. | |
| 9,254,961 B2 | 2/2016 | Kim | |
| 9,296,545 B2 | 3/2016 | Daniels et al. | |
| 9,299,210 B2 | 3/2016 | Parrish et al. | |
| 9,499,328 B2 | 11/2016 | Riedel et al. | |
| 9,688,471 B2 | 6/2017 | Hellenbrand | |
| 9,701,474 B2 | 7/2017 | Hellenbrand | |
| 9,745,131 B2 | 8/2017 | Hawkes et al. | |
| 9,932,176 B2 | 4/2018 | Hawkes et al. | |
| 10,007,764 B2 | 6/2018 | Kim | |
| 10,035,258 B2 | 7/2018 | Davis et al. | |
| 10,087,001 B2 | 10/2018 | Hellenbrand | |
| 2008/0235050 A1 * | 9/2008 | Hallberg | G06Q 30/06 |
| | | | 705/28 |
| 2010/0100393 A1 * | 4/2010 | Gourley | G06Q 30/02 |
| | | | 705/2 |
| 2010/0312578 A1 * | 12/2010 | Hardaway | G06Q 30/0207 |
| | | | 705/14.1 |
| 2013/0335563 A1 | 12/2013 | Jordan et al. | |
| 2018/0085287 A1 | 3/2018 | Kim | |
| 2019/0042701 A1 | 2/2019 | Wingenter et al. | |

* cited by examiner

CENTRAL FILL FACILITY AND ASSOCIATED DRUG DISPENSING SYSTEM AND METHOD

CROSS-REFERENCE TO A RELATED APPLICATION

The present application claims priority to U.S. Provisional Patent Application No. 62/415,942 filed Nov. 1, 2016, the contents of which are incorporated herein in their entirety.

TECHNOLOGICAL FIELD

An example embodiment relates generally to a central fill facility and an associated drug dispensing system and method and, more particularly, to a central fill facility and an associated drug dispensing system and method for dispensing drugs in a manner that permits drugs to be dispensed pursuant to a predefined program to be co-located with quantities of the same drug that are not to be dispensed pursuant to the predefined program.

BACKGROUND

A variety of different systems and facilities have been developed in order to efficiently and accurately dispense drugs or other medication. One example of a facility for dispensing medication is a central fill facility. A central fill facility may be operated by a pharmaceutical company, a drug distribution company or the like on behalf of a relatively large pharmacy or a pharmaceutical chain in order to efficiently receive, store and dispense many different medications for distribution to the respective pharmacies. Central fill facilities generally receive bulk quantities of medications, such as in bottles or other containers, to be dispensed in smaller quantities to patients. Thus, a central fill facility generally includes one or more dispensing stations for dispensing medication from the stock maintained by the central fill facility into smaller packages based upon a prescription submitted by the pharmacy. After having verified the accuracy of the dispensing operation, the package that includes the smaller quantity of medication may be shipped to the pharmacy or, in some instances, directly to the patient on behalf of the pharmacy. By filling the prescriptions for the pharmacy or the pharmaceutical chain at the central fill facility, however, the prescriptions may be filled in a more efficient manner and frequently in a more automated fashion then that otherwise provided at an on-site pharmacy location.

One type of medication that may be dispensed, such as at a central fill facility, is a medication that is eligible pursuant to a 340B drug discount program. The 340B drug discount program is a program created by the U.S. federal government that requires drug manufacturers to provide outpatient drugs to eligible health care organizations or covered entities at reduced prices. In a number of instances, one portion of a respective medication is eligible for dispensation pursuant to the 340B drug pricing program, while another portion of the same medication is ineligible for dispensation pursuant to the 340B drug pricing program and, instead, is to be dispensed and billed in a conventional manner, such as by being billed to the pharmacy at the time at which the medication is dispensed. Since the same medication is to be differently billed at the time of dispensing, it may be challenging or at least inefficient for medication dispensing systems, such as a central fill facility, to accurately account for the medication to be dispensed pursuant to a 340B drug pricing program.

In this regard, billing systems have been developed for medication to be dispensed and billed pursuant to the 340B medication dispensing program. At least some of these billing systems operate in a credit mode in which the covered entity is invoiced, the 340B eligible medication is virtually shipped to the pharmacy and the 340B eligible medication is then virtually returned by the pharmacy at a different cost, such as a retail cost. Even though the medication itself is not physically shipped and returned as part of this billing process, the virtual shipment and return are conducted in an effort to handle the different billing associated with a 340B eligible medication. However, this process is at least sometimes inefficient and undesirably consumes processing resources and memory space in order to track the invoicing and the virtual shipments and returns.

BRIEF SUMMARY

A central fill facility and a drug dispensing system and method are provided in accordance with an example embodiment in order to efficiently and accurately dispense a plurality of different drugs, including a drug for which some, but not all, is eligible to be dispensed pursuant to a predefined program, such as a drug discount program, e.g., a 340B drug pricing program. In this regard, the central fill facility as well as the associated drug dispensing system and method of an example embodiment are configured to prioritize the dispensing of the drug that is eligible for the predefined program relative to the dispensing of the same drug that is ineligible for predefined program. Further, the central fill facility as well as the medication dispensing system and method of an example embodiment differently bill upon the dispensing of the drug pursuant to the predefined program, such as a drug discount program, e.g., a 340B drug pricing program, such as by zero billing for the dispensing of the drug eligible for the predefined program, while billing in a more conventional fashion for the dispensing of the same drug that is ineligible for the predefined program.

In an example embodiment, a central fill facility is provided for filling prescriptions and dispensing drugs. The central fill facility includes a storage system configured to store a plurality of different drugs including a co-located inventory of a respective drug having both a first portion of the inventory of the respective drug to be dispensed pursuant to a predefined program, such as a drug discount program, e.g., a 340B drug pricing program, and a second portion of the inventory of the respective drug that is not to be dispensed pursuant to the predefined program. The central fill facility also includes the dispensing station configured to dispense drugs from the storage system into a respective package. The central fill facility further includes a transportation system comprising at least one of a conveyor belt or a robotic transport mechanism configured to receive the respective package from the dispensing station for transportation therefrom, such as by transporting a container into which the respective package is placed. Following receipt of the respective package from the transportation system, the central fill facility includes a verification station including an imaging system configured to capture and evaluate an image of the drugs dispensed into the respective package in order to verify an accuracy of the drugs dispensed in to the respective package prior to the shipment of the package. The central fill facility additionally includes dispensing control circuitry, such as a controller, configured to control the dispensing station so as to dispense the respective drug such that the first portion of the inventory of the respective drug to be dispensed pursuant to the predefined program is dispensed prior to dispensing the second portion of the inventory of the respective drug that is not to be dispensed pursuant to the predefined program.

The central fill facility of an example embodiment also includes a billing system configured to differently bill for dispensing of the respective drug depending upon whether the respective drug is dispensed pursuant to a 340B drug pricing program. In this regard, the billing system of an example embodiment is configured to zero bill for dispensing of the respective drug pursuant to the 340B drug pricing program. The storage system of an example embodiment is configured to receive the plurality of different drugs. In this regard, the first portion of the inventory of the respective drug to be dispensed pursuant to the 340B drug pricing program has been invoiced to a covered entity prior to receipt by the storage system.

In another example embodiment, a drug dispensing system is provided that includes a storage system configured to store a plurality of different drugs including a co-located inventory of a respective drug having both a first portion of the inventory of the respective drug to be dispensed pursuant to a predefined program, such as a drug discount program, e.g., a 340B drug pricing program, and a second portion of the inventory of the respective drug that is not to be dispensed pursuant to the predefined program. The drug dispensing system also includes the dispensing station configured to dispense drugs from the storage system into a respective package. The drug dispensing system additionally includes dispensing control circuitry, such as a controller, configured to control the dispensing station so as to dispense the respective drug such that the first portion of the inventory of the respective drug to be dispensed pursuant to the predefined program is dispensed prior to dispensing the second portion of the inventory of the respective drug that is not to be dispensed pursuant to the predefined program.

The drug dispensing system of an example embodiment also includes a billing system configured to differently bill for dispensing of the respective drug depending upon whether the respective drug is dispensed pursuant to a 340B drug pricing program. In this regard, the billing system of an example embodiment is configured to zero bill for dispensing of the respective drug pursuant to the 340B drug pricing program. The storage system of an example embodiment is configured to receive the plurality of different drugs. In this regard, the first portion of the inventory of the respective drug to be dispensed pursuant to the 340B drug pricing program has been invoiced to a covered entity prior to receipt by the storage system. The drug dispensing system of an example embodiment further includes a verification station configured to verify an accuracy of the drugs dispensed in to the respective package prior to the shipment of the package. For example, the verification system may include an imaging system configured to capture and evaluate an image of the drugs dispensed into the respective package in order to provide for verification. The drug dispensing system of an example embodiment is disposed within a central fill facility.

In a further example embodiment, a method for dispensing drugs is provided that includes storing a plurality of different drugs. The different drugs that are stored include a co-located inventory of a respective drug having both a first portion of the inventory of the respective drug to be dispensed pursuant to a predefined program, such as a drug discount program, e.g., a 340B drug pricing program, and a second portion of the inventory of the respective drug that is not to be dispensed pursuant to the predefined program. The method also includes dispensing drugs into a respective package. In this regard, the dispensing of the drugs includes controlling the dispensing of the drugs so as to dispense a respective drug such that the first portion of the inventory of the respective drug to be dispensed pursuant to the predefined program is dispensed prior to the dispensing the second portion of the inventory of the respective drug that is not to be dispensed pursuant to the predefined program. The method also includes verifying the accuracy of the drugs dispensed into the respective package prior to shipment of the package such as by capturing and evaluating an image of the drugs dispensed into the respective package.

The method of an example embodiment also includes differently billing for dispensing of the respective drug depending upon whether the respective drug is dispensed pursuant to a 340B drug pricing program. In this regard, the different billing includes zero billing for dispensing of the respective drug pursuant to the 340B drug pricing program. The method of an example embodiment also includes receiving a plurality of different drugs. The first portion of the inventory of the respective drug to be dispensed pursuant to the 340B drug pricing program has been invoiced to a covered entity prior to receipt by the storage system. In an example embodiment, the storing, dispensing and controlling are performed within a central fill facility.

BRIEF DESCRIPTION OF THE DRAWINGS

Having thus described certain example embodiments of the invention in general terms, reference will now be made to the accompanying drawings, which are not necessarily drawn to scale, and wherein:

DETAILED DESCRIPTION

The present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Further, the apparatus and method of example embodiments of the present invention will be primarily described in conjunction with medical-imaging applications. It should be understood, however, that the apparatus and method may be utilized in conjunction with a variety of other applications, both in the medical industry and outside the medical industry. Like numbers refer to like elements throughout.

A central fill facility as well as a drug dispensing system and method associated therewith are provided in accordance with an example embodiment. The drug dispensing system may be employed in a variety of different settings. A central fill facility may be operated by a pharmaceutical company, a drug distribution company or the like on behalf of one or more pharmacies, pharmaceutical chains or the like. The central fill facility efficiently and accurately fills prescriptions submitted by the pharmacy or pharmaceutical chain for which the central fill is operated, frequently with a level of automation that exceeds that provided by a typical pharmacy so as to increase the efficiency and accuracy with which the prescriptions are filled. Although described herein in conjunction with a central fill facility for purposes of example but not of limitation, the drug dispensing system and method of other embodiments may be deployed in other types of facilities.

A variety of different drugs or other medications are dispensed by the drug dispensing system and method. At least one of the drugs is eligible to be dispensed and billed pursuant to a predefined program, such as a drug discount program. By way of example of a drug discount program, a 340B drug pricing program will be discussed herein. However, the drugs may be dispensed in accordance with other embodiments of the present invention pursuant to other types of drug discount programs that provide for reduced prices for some, but not necessarily all, of the dispensed drugs. The 340B drug pricing program is a drug discount program created by the U.S. federal government that requires drug manufacturers to provide outpatient drugs to eligible healthcare organizations, covered entities, etc. (hereinafter generally referenced as a "covered entity") at reduced prices. The covered entities that are eligible for participation in the 340B drug pricing program as well as the patients that seek care from a covered entity that are eligible to receive outpatient prescription drugs at 340B discounted prices are defined by the federal legislation that established and implemented the 340B drug discount program. By way of example, covered entities include not-for-profit hospitals owned or operated by or under contract with a state or local government as well as certain federally qualified health centers.

Figure 1:
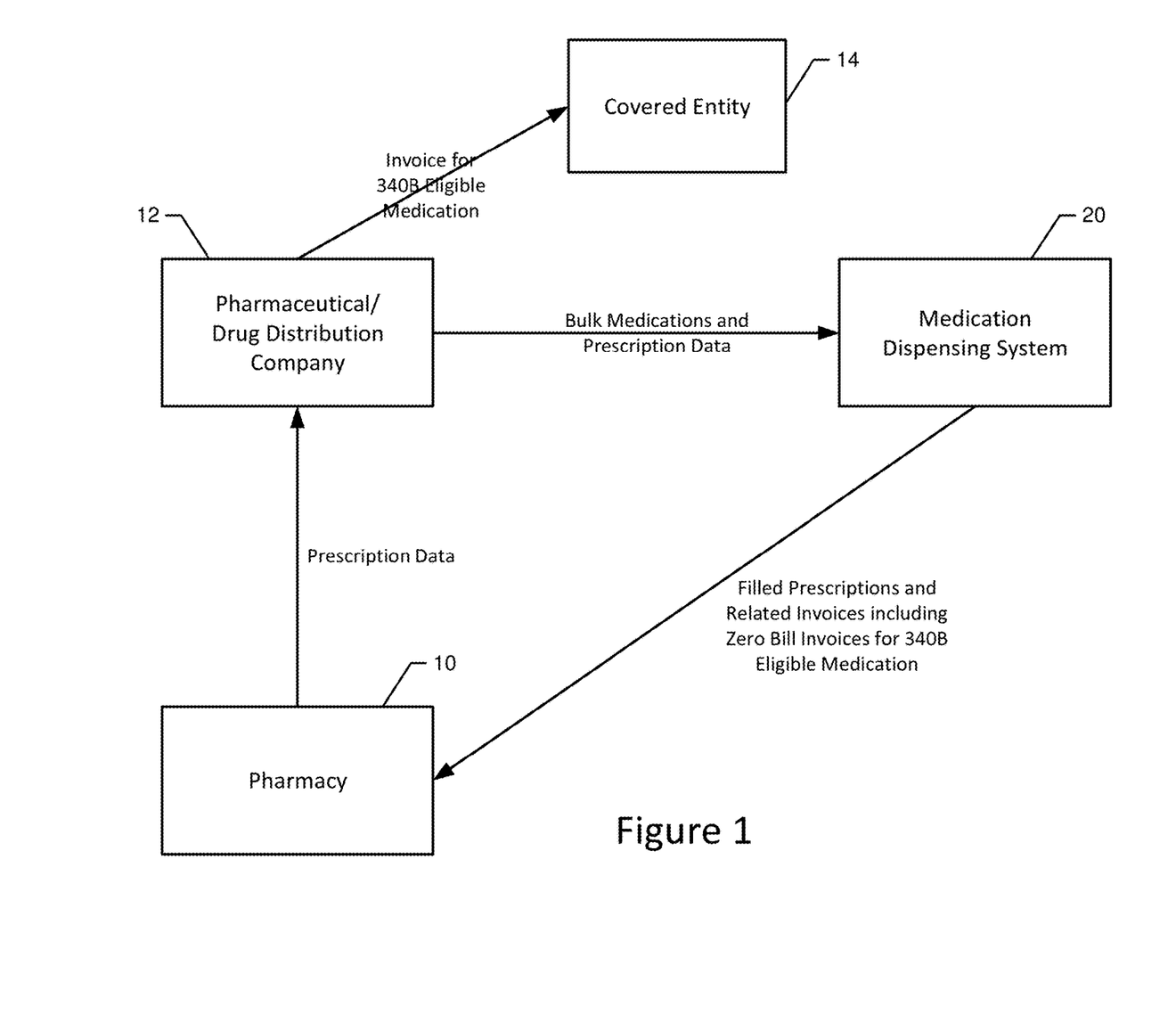
FIG. 1 is an overview of the parties involved in a drug dispensing process in accordance with an example embodiment of the present disclosure.

In relation to the drugs received and stored by a drug dispensing system, such as a central fill, a pharmacy 10 submits prescription data to a third party processor, such as a pharmaceutical company 12, a drug distribution company or the like, as shown in FIG. 1. The prescription data is tested for eligibility for the 340B drug pricing program in order to identify drug that qualifies, that is, is eligible, for dispensing and billing pursuant to the 340B drug pricing program. The pharmaceutical company, the drug distribution company or the like then ships the drugs, including the drug eligible under the 340B drug pricing program, that was identified by the prescription data submitted by the pharmacy along with the prescription data or related prescription information to the drug dispensing facility 20, such as the central fill, such as on a daily or other periodic basis. With respect to the drug that is eligible for the 340B drug pricing program, the pharmaceutical company, the drug distribution company or the like may maintain a count, such as in an accumulator, of the quantity of the drug that is eligible for the 340B drug pricing program and may ship the drug to the drug dispensing facility, such as the central fill, once a predefined quantity has been requested and deemed eligible, such as the quantity of the drug contained in the bulk packaging utilized by the pharmaceutical company, the drug distribution company or the like. For those drugs identified to be eligible for the 340B drug pricing program, the covered entity 14 is invoiced or billed for the drug eligible for the 340B drug pricing program when the drug eligible for the 340B drug pricing program is shipped to the drug dispensing system, such as the central fill facility.

As described below and at the central fill facility, the drugs are dispensed from the bulk packaging in which the drugs were received from the pharmaceutical company 12, the drug distribution company or the like to smaller packages that fulfill individual prescriptions by respective patients of the pharmacy 10. As also described below, the drug that is eligible for the 340B drug pricing program is prioritized in terms of its dispensing such that the same drug that is eligible for the 340B drug pricing program is dispensed prior to dispensing of the same drug that is not eligible for the 340B drug pricing program. Upon dispensing the drug, the pharmaceutical company operating the drug dispensing system 20, such as the central fill, for the pharmacy then bills the pharmacy for all of the dispensed drug. For the drug that is dispensed that is eligible for the 340B drug pricing program, the pharmacy is billed in a different manner than the other drugs, such as by being zero billed for the drug that is eligible for the 340B drug pricing program (other than an optional fee allocated on a per prescription basis, e.g., X dollars per prescription, that is not dependent upon the price of the drug itself), since the covered entity has already been billed for the same drug. Thereafter, the packages into which the drugs have been dispensed are shipped, typically to the pharmacy.

Figure 2:
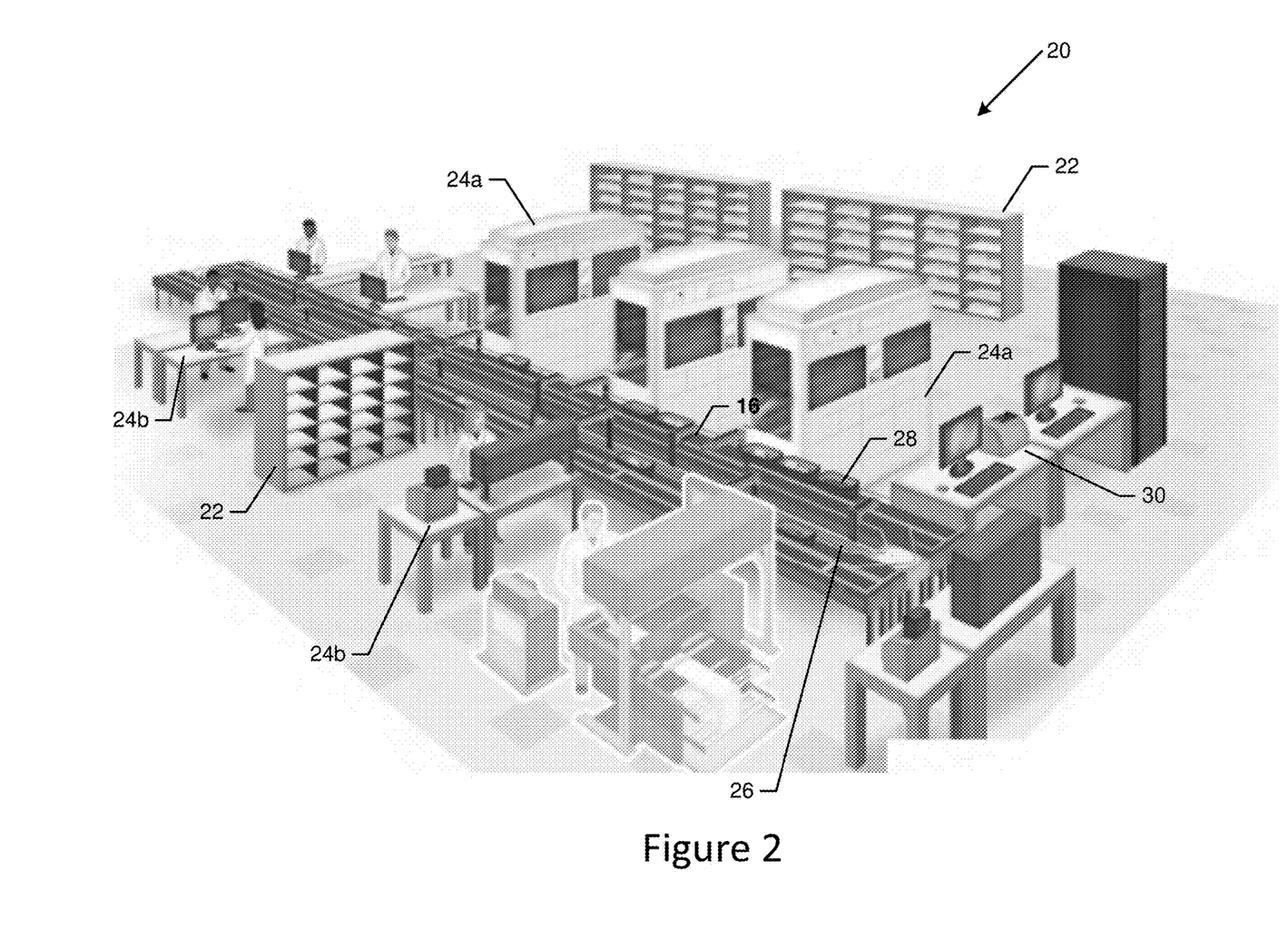
FIG. 2 is a perspective view of a central fill facility and may be operated in accordance with an example embodiment of the present disclosure.

As shown in FIG. 2, a drug dispensing system 20 in the form of a central fill is depicted. However, the drug dispensing system may be configured in a variety of different manners in other embodiments. The drug dispensing system includes a storage system 22 configured to store a plurality of different drugs. Typically, the drugs are packaged in a bulk form, such as in larger bottles or containers with greater counts, such as with many more pills, than typically dispensed to an individual patient. The storage system may take various forms including shelves, bins, racks or the like.

Among the drugs stored by the storage system 22 is at least one drug for which a portion of the drug is eligible pursuant to the 340B drug pricing program and another portion of the same drug is ineligible for the 340B drug pricing program. Thus, the storage system is configured to store co-located inventory of a respective drug having both a first portion of the inventory of the respective drug to be dispensed pursuant to the 340B drug pricing program and a second portion of the inventory of the respective drug that is not to be dispensed pursuant to the 340B drug pricing program. Typically, the storage system does not physically distinguish between the two different portions of the same drug and, instead, the drug dispensing system 20, such as dispensing control circuitry 32, e.g., a controller as described below, tracks the portion of the inventory of the respective drug that is to be dispensed pursuant to the 340B drug pricing program and the other portion of the drug that is not to be dispensed pursuant to the 340B drug pricing program. For example, the storage system may store 10 bottles of the same drug of the same size and of the same strength with each bottle including 300 pills. Of these bottles, four bottles are eligible to be dispensed pursuant to the 340B drug pricing program as a result of the submittal of prescription data by the pharmacy for which 1200 pills were deemed to be eligible for the 340B drug pricing program, while the other six bottles of pills are ineligible for the 340B drug pricing program.

For those drugs that are eligible to be dispensed pursuant to the 340B drug pricing program, the drug has been previously billed or invoiced to a covered entity prior to receipt by the storage system 22. However, the other drugs including the same drug that is ineligible for the 340B drug pricing program have not generally been billed or invoiced prior to receipt of the storage system. Thus, for the co-located inventory of the respective drug, the first portion of the respective drug that is eligible for the 340B drug pricing program is owned by the covered entity 14 and held by the pharmaceutical company 12 at the central fill on behalf of the covered entity, since the covered entity was invoiced for the 340B eligible drug at the time of shipment to the central fill. Conversely, the second portion of the respective drug that is ineligible for the 340B drug pricing program continues to be owned by the pharmaceutical company until the second portion of the drug is dispensed and shipped to the pharmacy 10, since neither the pharmacy nor any other entity, is invoiced for the 340B ineligible drug until the drug has been dispensed and at the time of shipment to the pharmacy.

Figure 3:
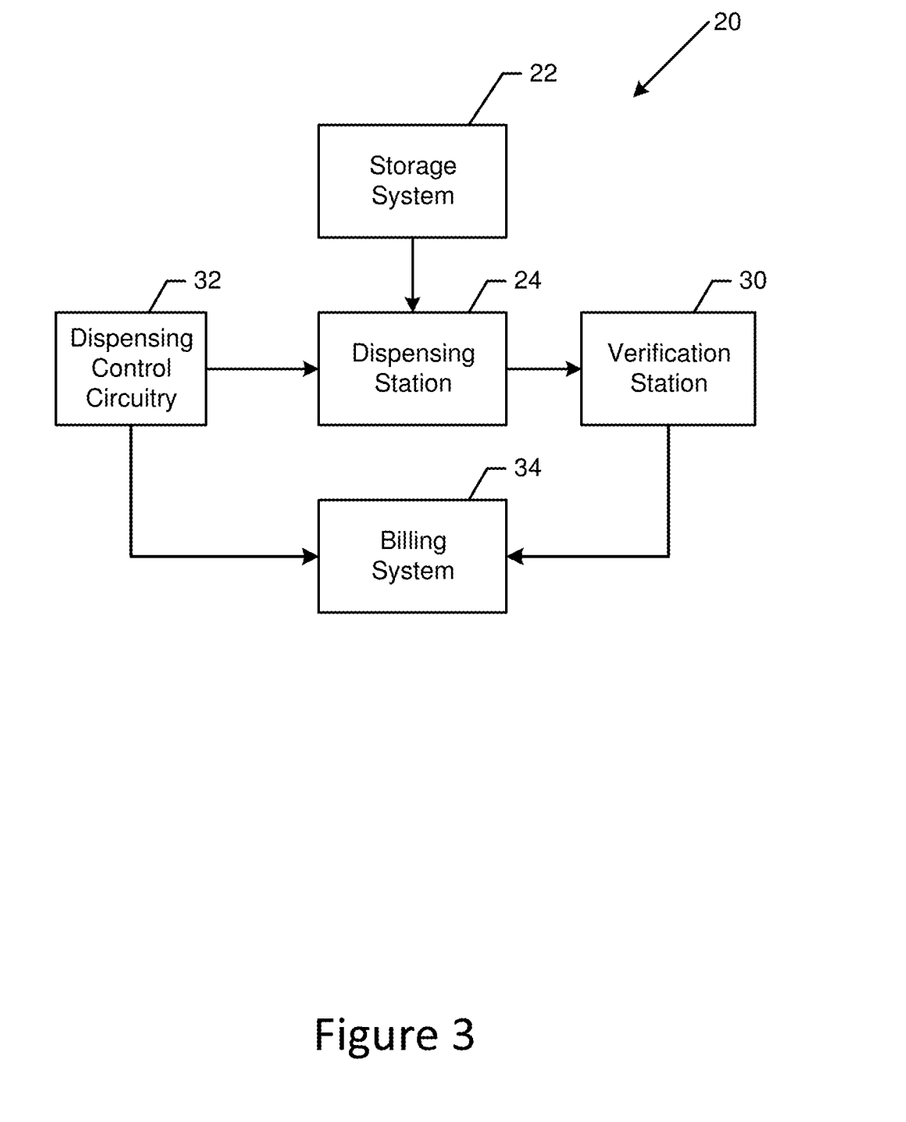
FIG. 3 is a block diagram of a drug dispensing system in accordance with an example embodiment of the present disclosure.

The drug dispensing system 20 also includes a dispensing station 24 configured to dispense drugs from the storage system 12 into a respective package. As shown in FIG. 3, the dispensing station is responsive to the storage system as a result of its receipt of drugs from the storage system. In this regard, the drugs may be manually transferred from the storage system to the dispensing station. Alternatively, the drug dispensing system may be more greatly automated such that all or at least some of the drugs are robotically transferred or otherwise transferred in an automated fashion from the storage system to the dispensing station. The drug dispensing system may include a plurality of dispensing stations, some of which include automated dispensing stations 24a and some of which include manual dispensing stations 24b, typically depending upon the type of drugs to be dispensed and the level of automation of the drug dispensing system. In regards to an automated dispensing station, an automated dispensing station may be embodied in various manners including, for example, as described by U.S. Patent Application Publication No. US 2013/0335563 to Michael Lee Jordan, et al., the contents of which are incorporated herein by reference in their entirety.

As shown in FIG. 3, the drug dispensing system 20 also includes dispensing control circuitry 32, such as a controller, configured to control the dispensing station 24. The controller may be configured in various manners, but, in an example embodiment, it is embodied by a computing device, such as a computer workstation, a personal computer, a mobile or smartphone, a desktop computer, a tablet computer, a notebook computer, a laptop computer, a distributed system, a server, a blade, a gateway, a switch, a processing device, or combination of processing devices adapted to perform the functions described herein.

In one embodiment, the controller may include a processor that communicates with other elements of the controller via a system interface or bus. The processor may be embodied in a number of different ways. For example, the processor may be embodied as a processing element, processing circuitry, a coprocessor, a controller or various other processing devices including integrated circuits such as, for example, an application specific integrated circuit (ASIC), a field programmable gate array (FPGA), a hardware accelerator, and/or the like. In an example embodiment, the processor may be configured to execute instructions stored in memory or otherwise accessible to the processor. As such, whether configured by hardware or software methods, or by a combination thereof, the processor may represent an entity capable of performing operations according to embodiments of the present invention when configured accordingly.

The controller may further include a memory device, such as a non-transitory memory device, which may include both random access memory (RAM) and read only memory (ROM). The ROM may be used to store a basic input/output system (BIOS) containing the basic routines that help to transfer information to the different elements within the controller. A number of executable instructions, applications, scripts, program modules, and/or the like may be stored by the memory device. These executable instructions, applications, program modules, and/or the like may control certain aspects of the operation of the controller with the assistance of the processor and operating system. In addition to the program modules, the controller may store or be in communication with one or more databases.

Regardless of the manner in which the dispensing control circuitry 32, such as the controller, is embodied, the dispensing control circuitry is configured to control the dispensing station 24 so as to dispense the respective drug, that is, the drug for which some, but not all, is eligible to be dispensed and billed pursuant to the 340B drug pricing program, such that the first portion of the inventory of the respective drug to be dispensed pursuant to the 340B drug pricing program is dispensed prior to dispensing the second portion of the inventory of the same respective drug that is ineligible and therefore not to be dispensed pursuant to the 340B drug pricing program. In the foregoing example in which the storage system stored 10 bottles of a particular drug with each bottle including 300 pills and with four of the bottles eligible for the 340B drug pricing program and six of the bottles being ineligible for the 340B drug pricing program, in an instance in which the prescriptions to be filled by the drug dispensing system on behalf of the pharmacy equate to the dispensing of 1500 pills, the four bottles of pills that are eligible for the 340B drug pricing program would initially be dispensed with the pills repackaged into a plurality of typically smaller packages, each of which is associated with the fulfillment of an individual prescription, followed by the dispensing of one of the bottles of the pills that are ineligible for the 340B drug pricing program. As such, the dispensing of the drug that is eligible for the 340B drug pricing program is prioritized relative to the dispensing of the same drug that is ineligible for the 340B drug pricing program.

The drug dispensing system 20 further includes a verification station 30 downstream of the dispensing station 24 and configured to verify the accuracy of the drugs dispensed into the respective package prior to shipment of the package. The package into which the drugs are dispensed may be transported from the dispensing station to the verification station in various manners. In the embodiment illustrated in FIG. 2, the drug dispensing system includes a transportation system including a network of conveyor belts 26 and/or robotic transport mechanism for transporting the tote or other container 28 into which the package into which the drugs are dispensed is placed from the dispensing station to the verification station. The verification station may be manual, such as in terms of a technician visually reviewing the contents of the package prior to shipment, automated, such as in terms of an imaging system configured to capture and evaluate an image of the drugs dispensed into the respective package in order to verify the accuracy of the contents prior to shipment of the package, or semi-automated relying in part upon computer vision and, in part upon manual inspection. If the accuracy of the drugs dispensed into the respective package is verified, both in terms of the quantity of the drugs and the identity of the drugs, the package may then be shipped, typically to the pharmacy to be picked up by the patient. Alternatively, if the package is not verified, the package may be rejected and the prescription(s) contained within the package may be reworked.

The drug dispensing system 20 may also include a billing system 34 as shown in FIG. 3. The billing system may be embodied in various manners including, for example, by a computing device, such as a computer workstation, a personal computer, a mobile or smartphone, a desktop computer, a tablet computer, a notebook computer, a laptop computer, a distributed system, a server, a blade, a gateway, a switch, a processing device, or combination of processing devices adapted to perform the functions described herein.

In one embodiment, the billing system 34 may include a processor that communicates with other elements of the dispensing control circuitry 32, such as a controller, via a system interface or bus. The processor may be embodied in a number of different ways. For example, the processor may be embodied as a processing element, processing circuitry, a coprocessor, a controller or various other processing devices including integrated circuits such as, for example, an ASIC, an FPGA, a hardware accelerator, and/or the like. In an example embodiment, the processor may be configured to execute instructions stored in memory or otherwise accessible to the processor. As such, whether configured by hardware or software methods, or by a combination thereof, the processor may represent an entity capable of performing operations according to embodiments of the present invention when configured accordingly.

The billing system 34 may further include a memory device, such as a non-transitory memory device, which may include both RAM and ROM. The ROM may be used to store the BIOS containing the basic routines that help to transfer information to the different elements within the billing system. A number of executable instructions, applications, scripts, program modules, and/or the like may be stored by the memory device. These executable instructions, applications, program modules, and/or the like may control certain aspects of the operation of the billing system with the assistance of the processor and an operating system.

Regardless of the manner in which the billing system 34 is embodied, the billing system is generally configured to bill, e.g., issue an invoice to, the pharmacy upon dispensation of the drugs. However, the billing system of this example embodiment is configured to differently bill for the dispensing of the respective drug, that is, the drug for which a portion is eligible for the 340B drug pricing program, depending upon whether or not the respective drug is dispensed pursuant to the 340B drug pricing program. In this regard, the billing system is configured to bill a reduced amount (relative to the same drug that is not dispensed pursuant to the 340B drug pricing program). For example, the billing system of an example embodiment is configured to zero bill, that is, to issue an invoice for zero dollars (other than an optional fee allocated on a per prescription basis that is independent of the cost of the drug itself as noted above), for dispensing of the respective drug that is eligible pursuant to the 340B drug pricing program. Since the drug that is dispensed pursuant to the 340B drug pricing program was previously billed to the covered entity, the issuance of a bill for a reduced amount, such as a zero bill, avoids duplicate invoicing and payment for the same drug. However, for the dispensing of the same drug that is ineligible for the 340B drug pricing program, the billing system is generally configured to generate bills or invoices for the drug in a conventional manner, such as by billing the pharmacy for the cost of the drug that is dispensed, thereby generating a bill for an amount greater than the reduced amount charged for the same drug dispensed pursuant to the 340B drug pricing program.

In operation, a plurality of different drugs are stored, such as by the storage system 22. See block 40 of FIG. 4. The plurality of different drugs that are stored include a co-located inventory of every respective drug having both a first portion of the inventory of the respective drug that is to be dispensed pursuant to the 340B drug pricing program and a second portion of the inventory of the respective drug that is not to be dispensed pursuant to the 340B drug pricing program. As to the stored drugs, the plurality of different drugs are received by the storage system with the first portion of the inventory of the respective drug to be dispensed pursuant to the 340B drug pricing program having been previously billed to a covered entity prior to receipt by the storage system.

Figure 4:
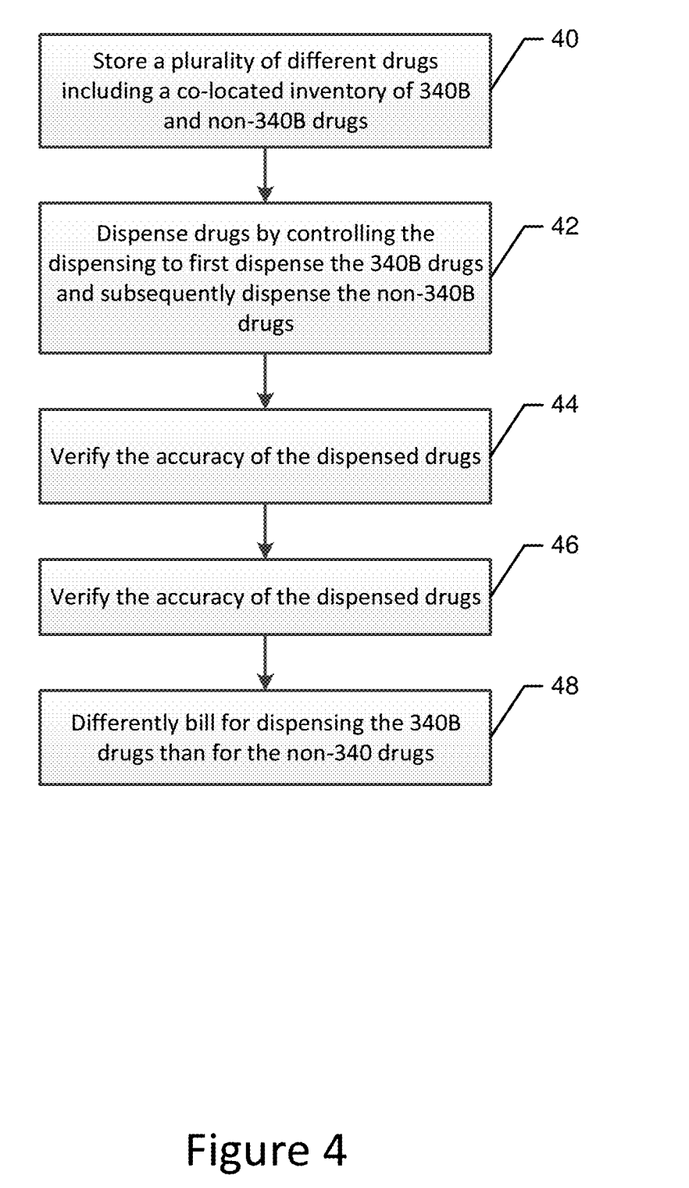
FIG. 4 is a flowchart illustrating operations performed, such as by the drug dispensing system of FIG. 3, in accordance with an example embodiment of the present disclosure.

As shown in block 42 of FIG. 4, the method also includes dispensing drugs into a respective package. In this regard, the dispensing of the drugs is controlled such that the first portion of the inventory of the respective drug to be dispensed pursuant to the 340B drug pricing program is dispensed prior to dispensing the second portion of the inventory of the respective drug that is not to be dispensed pursuant to the 340B drug pricing program. Thereafter, the dispensed drugs are transported from the dispensing station 24 to the verification station 30 at which the accuracy of the drugs dispensed into the respective package is verified prior to shipment of the package, such as to the pharmacy that submitted the prescription. See blocks 44 and 46 of FIG. 4. As shown in block 48 of FIG. 4, the method of an example embodiment also includes differently billing for dispensing of the respective drug depending upon whether the respective drug is dispensed pursuant to the 340B drug pricing program. In an example embodiment, the different billing includes billing a reduced amount, such as zero billing, for dispensing of the respective drug pursuant to the 340B drug pricing program, while billing a greater amount, such as by billing in a more conventional manner upon the dispensing of the same drug that is ineligible for the 340B drug pricing program.

As described above, a drug dispensing system 20 and method are therefore provided in order to efficiently and accurately dispense a plurality of different drugs, such as in a central fill facility, including a drug for which some, but not all, is eligible to be dispensed pursuant to a 340B drug pricing program. In this regard, the drug dispensing system and method are configured to prioritize the dispensing of the drug that is eligible for the 340B drug pricing program relative to the dispensing of the same drug that is ineligible for the 340B drug pricing program. Further, the drug dispensing system and method differently bill upon the dispensing of the drug pursuant to the 340B drug pricing program, such as by billing a reduced amount, such as by zero billing, for the dispensing of the drug eligible for the 340B drug pricing program, while billing a greater amount, such as by billing in a more conventional fashion for the dispensing of the same drug that is ineligible for the 340B drug pricing program. As such, the drug dispensing system and method permit 340B eligible drugs to be dispensed in an efficient manner that reduces the consumption of the processing resources and memory space otherwise expended to track the invoicing and the virtual shipments and returns of 340B eligible drugs.

As described above, aspects of the drug dispensing system 20, such as the control of the dispensation of the drugs, may be implemented by various means, such as hardware and/or a computer program product comprising one or more computer-readable mediums having computer readable program instructions stored thereon. For example, the control of the dispensing of the drugs by the dispensing control circuitry 32, such as the controller, described herein may be embodied by computer program instructions of a computer program product. In this regard, the computer program product(s) which embody the procedures described herein may be stored by one or more memory devices of a computing device and executed by a processor, of the computing device. In some embodiments, the computer program instructions comprising the computer program product(s) which embody the procedures described above may be stored by memory devices of a plurality of computing devices. As will be appreciated, any such computer program product may be loaded onto a computer or other programmable apparatus to produce a machine, such that the computer program product including the instructions which execute on the computer or other programmable apparatus creates means for implementing the. Further, the computer program product may comprise one or more computer-readable memories on which the computer program instructions may be stored such that the one or more computer-readable memories can direct a computer or other programmable apparatus to function in a particular manner, such that the computer program product comprises an article of manufacture which implements the control over the dispensing of the drugs. The computer program instructions of one or more computer program products may also be loaded onto a computer or other programmable apparatus to cause a series of operations to be performed on the computer or other programmable apparatus to produce a computer-implemented process such that the instructions which execute on the computer or other programmable apparatus implement the control over the dispensing of the drugs.

Blocks or steps of the flowchart of FIG. 4 support combinations of means for performing the specified functions and combinations of steps for performing the specified functions. It will also be understood that one or more blocks of the flowchart, and combinations of blocks in the flowchart, may be implemented by special purpose hardware-based computer systems which perform the specified functions or steps, or combinations of special purpose hardware and computer program product(s).

The above described functions may be carried out in many ways. For example, any suitable means for carrying out each of the functions described above may be employed to carry out embodiments of the invention. In one embodiment, a suitably configured processor may provide for control over the dispensing of the drugs. In another embodiment, a computer program product may provide for control over the dispensing of the drugs and may include a computer-readable storage medium, such as the non-volatile storage medium, and computer-readable program code portions, such as a series of computer instructions, embodied in the computer-readable storage medium.

Many modifications and other embodiments of the inventions set forth herein will come to mind to one skilled in the art to which these inventions pertain having the benefit of the teachings presented in the foregoing descriptions and the associated drawings. Therefore, it is to be understood that the embodiments of the invention are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

What is claimed is:

1. A central fill facility for filling prescriptions and dispensing drugs, the central fill facility comprising:
    a storage system configured to receive and store a plurality of different drugs including a co-located inventory of a respective drug having both a first portion of the inventory of the respective drug to be dispensed pursuant to a predefined discount program and a second portion of the inventory of the respective drug that is not to be dispensed pursuant to the predefined discount program, wherein a cost associated with the first portion of inventory of the respective drug has been previously billed to a covered entity associated with the predefined discount program prior to receipt by the storage system;
    an automated dispensing station configured to dispense drugs from the storage system into a respective package;
    a transportation system comprising at least one of a conveyor belt or a robotic transport mechanism, wherein the transportation system is configured to receive the respective package from the dispensing station for transportation therefrom;
    following receipt of the respective package from the transportation system, a verification station comprising an imaging system configured to capture and evaluate an image of the respective drugs dispensed into the respective package in order to verify an accuracy of the drugs dispensed into the respective package prior to shipment of the package;
    dispensing control circuitry configured to control the automated dispensing station so as to distinguish between and prioritize dispensing of the respective drug from the first portion of the inventory of the respective drug to be dispensed pursuant to the predefined discount program relative to dispensing of the respective drug from the second portion of the inventory of the respective drug that is not to be dispensed pursuant to the predefined discount program; and
    a billing system configured to differently bill for the dispensing of the first portion of the inventory of the respective drug to be dispensed pursuant to the predefined discount program and the dispensing of the second portion of the inventory of the respective drug that is not to be dispensed pursuant to the predefined discount program, wherein the billing system is configured to zero bill for the dispensing of the first portion of the inventory of the respective drug to be dispensed pursuant to the predefined discount program, and to bill another amount for the dispensing of the second portion of the inventory of the respective drug that is ineligible for the predefined discount program.

2. A central fill facility in accordance with claim 1 wherein the transportation system is configured to transport a container into which the respective package is placed from the dispensing station to the verification station.

3. A drug dispensing system comprising:
a storage system configured to receive and store a plurality of different drugs including a co-located inventory of a respective drug having both a first portion of the inventory of the respective drug to be dispensed pursuant to a predefined discount program and a second portion of the inventory of the respective drug that is not to be dispensed pursuant to the predefined discount program, wherein a cost associated with the first portion of the inventory of the respective drug has been previously billed to a covered entity associated with the predefined discount program prior to receipt by the storage system;
an automated dispensing station configured to dispense drugs from the storage system into a respective package;
dispensing control circuitry configured to control the automated dispensing station so as to distinguish between and prioritize dispensing of the respective drug from the first portion of the inventory of the respective drug to be dispensed pursuant to the predefined discount program relative to dispensing of the respective drug from the second portion of the inventory of the respective drug that is not to be dispensed pursuant to the predefined discount program; and
a billing system configured to differently bill for the dispensing of the first portion of the inventory of the respective drug to be dispensed pursuant to the predefined discount program and the dispensing of the second portion of the inventory of the respective drug that is not to be dispensed pursuant to the predefined discount program, wherein the billing system is configured to zero bill for the dispensing of the first portion of the inventory of the respective drug to be dispensed pursuant to the predefined discount program, and to bill another amount for the dispensing of the second portion of the inventory of the respective drug that is ineligible for the predefined discount program.

4. A drug dispensing system in accordance with claim 3 further comprising a verification station configured to verify an accuracy of the drugs dispensed into the respective package prior to shipment of the package.

5. A drug dispensing system in accordance with claim 4 wherein the verification station comprising an imaging system configured to capture and evaluate an image of the drugs dispensed into the respective package prior to shipment of the package.

6. A drug dispensing system in accordance with claim 3 further comprising a transportation system configured to receive the respective package from the dispensing station for transportation therefrom.

7. A drug dispensing system in accordance with claim 6 wherein the transportation system comprises at least one of a conveyor belt or a robotic transport mechanism configured to receive the respective package from the dispensing station for transportation therefrom.

8. A drug dispensing system in accordance with claim 3 wherein the drug dispensing system is disposed within a central fill facility.

9. A method for dispensing drugs comprising:
receiving and storing a plurality of different drugs including a co-located inventory of a respective drug having both a first portion of the inventory of the respective drug to be dispensed pursuant to a predefined discount program and a second portion of the inventory of the respective drug that is not to be dispensed pursuant to the predefined discount program, wherein a cost associated with the first portion of the inventory of the respective drug has been previously billed to a covered entity associated with the predefined discount program prior to receipt by the storage system;
dispensing drugs in an automated fashion into a respective package, wherein dispensing the drugs comprises controlling the automated dispensing of the drugs with dispensing control circuitry to distinguish between and prioritize dispensing of the respective drug from the first portion of the inventory of the respective drug to be dispensed pursuant to the predefined discount program relative to dispensing of the respective drug from the second portion of the inventory of the respective drug that is not to be dispensed pursuant to the predefined discount program;
capturing and evaluating an image of the respective drugs dispensed in order to verify an accuracy of the respective drugs dispensed into the respective package prior to shipment of the package; and
differently billing for the dispensing of the first portion of the inventory of the respective drug to be dispensed pursuant to the predefined discount program and the dispensing of the second portion of the inventory of the respective drug that is not to be dispensed pursuant to the predefined discount program, wherein differently billing comprises zero billing for the dispensing of the first portion of the inventory of the respective drug to be dispensed pursuant to the predefined discount program, and to bill another amount for the dispensing of the second portion of the inventory of the respective drug that is ineligible for the predefined discount program.

10. A method in accordance with claim 9 wherein the storing, dispensing, image capture and evaluation and controlling are performed within a central fill facility.

* * * * *

UNITED STATES PATENT AND TRADEMARK OFFICE
CERTIFICATE OF CORRECTION

PATENT NO. : 11,386,390 B2
APPLICATION NO. : 15/476091
DATED : July 12, 2022
INVENTOR(S) : Stump et al.

It is certified that error appears in the above-identified patent and that said Letters Patent is hereby corrected as shown below:

On the Title Page

Item (71) Applicant: "McKesson Corporation, San Francisco, CA (US)" should read --McKesson Corporation, Irving, TX (US)--.

Signed and Sealed this
Twenty-fifth Day of July, 2023

Katherine Kelly Vidal
*Director of the United States Patent and Trademark Office*